United States Patent [19]
Ota et al.

[11] Patent Number: 5,336,162
[45] Date of Patent: Aug. 9, 1994

[54] MEDICAL BANDAGE AND METHOD FOR USING THE SAME

[75] Inventors: Junzo Ota, Nishinomiya; Hajime Mura; Toshihiko Kawachi, both of Sakai, all of Japan

[73] Assignee: Kyowa Limited, Osaka, Japan

[21] Appl. No.: 133,334

[22] Filed: Oct. 8, 1993

[30] Foreign Application Priority Data

Jun. 18, 1993 [JP] Japan .................. 5-172671

[51] Int. Cl.$^5$ .................................. A61F 13/00
[52] U.S. Cl. .................................. 602/41; 602/57; 602/58
[58] Field of Search ............ 602/41, 42, 43, 44, 602/45, 46, 54, 57, 58; 128/887, 888, 889

[56] References Cited

U.S. PATENT DOCUMENTS

| | | | |
|---|---|---|---|
| 4,614,183 | 9/1986 | McCracken | 602/57 |
| 4,706,662 | 11/1987 | Thompson | 602/57 |
| 4,753,232 | 6/1988 | Ward | 602/57 |
| 4,832,008 | 5/1989 | Gilman | 602/57 |
| 5,052,381 | 10/1991 | Gilbert | 602/57 |
| 5,188,124 | 2/1993 | Feret | 602/58 |
| 5,213,565 | 5/1993 | Rollband | 602/58 |

*Primary Examiner*—Michael A. Brown
*Attorney, Agent, or Firm*—Armstrong, Westerman, Hattori, McLeland & Naughton

[57] ABSTRACT

A medical bandage that permits the support to be easily peeled off from the substrate without the substrate stuck to the wound skin being pulled up. It is composed of a substrate 1, a support 5 consisting of butted two pieces of plastics film having at least one extension part 5a extending beyond the end 1a of the substrate 1, and a releasable strip 8 of plastics adhesive tape stuck to the butting part 6, said adhesive tape having non-adhesive side parts.

9 Claims, 1 Drawing Sheet

MEDICAL BANDAGE AND METHOD FOR USING THE SAME

FIELD OF INDUSTRIAL APPLICATION

The present invention relates to a medical bandage and a method for applying it to a patient, said medical bandage being designed to be applied to burned, injured, or inflamed skins of a human and/or animal body for their protection or to be used to fix a medical instrument (such as catheter) on the skin.

PRIOR ART

A bandage is generally used to protect burned, injured, or inflamed skins or to fix a medical instrument (such as catheter) on the skin. Such a bandage has an adherent property and high permeability to oxygen and water vapor or has impermeability to water vapor so as to prevent the skin from drying. In addition, it has to fully conform to the contour of the body part to be covered. Moreover, it has to be very thin in the form of film or foil because it is applied directly to the skin. Such a thin bandage, however, involves difficulties in its application, in particular if large surface areas are to be covered, in which case it is liable to wrinkle and stick to itself.

In order to overcome these difficulties, there have been proposed several thin film-like or foil-like bandages and methods for applying them to patients. For example, U.S. Pat. No. 4,372,303 discloses a bandage which is provided on its back side with a stiffening frame as a means to assist its application which is removed after its application. This proposal may be useful for bandages to cover a relatively large flat part. However, the stiffening frame is inconvenient to applying the bandage to curved body parts. In addition, the stiffening frame obstructs the visual field.

To solve this problem, U.S. Pat. No. 4,374,520 proposed a bandage having two supporting ledges only at the longitudinally opposed edges. However, such a bandage cannot be used under all circumstances due to the stiff ledges and the obstructed visual field.

A bandage free of the foregoing disadvantages is disclosed in European Patent No. 51,935. It is composed of a film substrate and a support attached to its back, said support being stiffer than the film substrate and extending beyond one edge of the film substrate, the extended end serving as a grasp strip. This bandage has its adhesive layer covered with release paper which also extends beyond one edge of the film substrate, the extended end serving as a grasp strip. The support is removed after the bandage has been applied, with the release paper peeled off. Such an invention offers an advantage that the substrate is kept clean and free from wrinkling and curling owing to the support placed thereon and that the support does not obstruct the visual field. However, it does not necessarily solve all the problems. For example, it is necessary to peel off the support from one end of the substrate after the bandage has been applied to a patient. This incurs a possibility of the applied substrate being peeled off. In addition, when the release paper is removed, there is a possibility that the adhesive layer sticks to each other because the support is provided with only one grasp strip.

A certain solution to this problem was made by U.S. Pat. No. 4,619,253 (corresponding to Japanese Patent Publication No. 168450/1985). It discloses a bandage composed of a substrate, support, and release paper, said support covering entirely the back of the substrate and having grasp strips at its both ends, and said release paper having a zigzag cut line at its center in its longitudinal direction. This bandage is improved in the peeling of the release paper although it has a complicated structure, because the release paper can be easily pulled up at its center and removed in the direction toward its side edges. However, it still has the same disadvantage as the bandage of European Patent No. 51,935 mentioned above.

PROBLEM TO BE SOLVED BY THE INVENTION

The conventional bandages mentioned above have their respective disadvantages, particularly in the difficulty of peeling off the support from the substrate without causing the applied bandage to be peeled off.

The present invention was completed to solve this problem. Accordingly, it is an object of the present invention to provide a medical bandage which is capable of easy application without wrinkling to the wound skin and is constructed such that the support can be easily peeled off from the substrate without pulling up the substrate while it protects the bandage from dust and dirt during storage and the release paper can be easily peeled off from the substrate at the time of application.

The present invention is embodied in an improved medical bandage of the type having a substrate of plastic film or foil, a pressure-sensitive adhesive layer formed on said substrate, and a release paper placed on said pressure-sensitive adhesive layer, with one end thereof extending beyond the substrate to form an extension part and with the other end thereof holding thereunder a grasp strip which is partly in contact with the pressure-sensitive adhesive layer over a certain length from the end of the substrate, with the remainder folded back outward, wherein the improvement comprises a support and a releasable strip for the support, said support being composed of two sheets of plastics film butted in the widthwise direction, with at least one end thereof extending beyond the end of the substrate to form an extension part, said support being peelably fusion-bonded to the substrate except for the butting part, said releasable strip being an adhesive tape of desired width stuck to the butting part in the same direction as the butting part, said adhesive tape having non-adhesive parts on its both longitudinal sides.

The present invention is characterized in that the substrate is provided with a support which is peelably fusion-bonded to the substrate. This support protects the substrate from dust and dirt during storage and reinforces the substrate at the time of application so as to permit the release paper to be easily peeled off from the substrate of thin film or foil. Moreover, the support is composed of two pieces of plastics film which are butted, and the butting part is covered with a releasable strip. This construction permits the support to be separated from the butting part and to be peeled easily from the substrate after the bandage has been applied to a patient. The support can be peeled off without the possibility of pulling up the substrate of thin film or foil which has been applied to a patient.

DETAIL DESCRIPTION OF THE DRAWINGS

Figure 1:
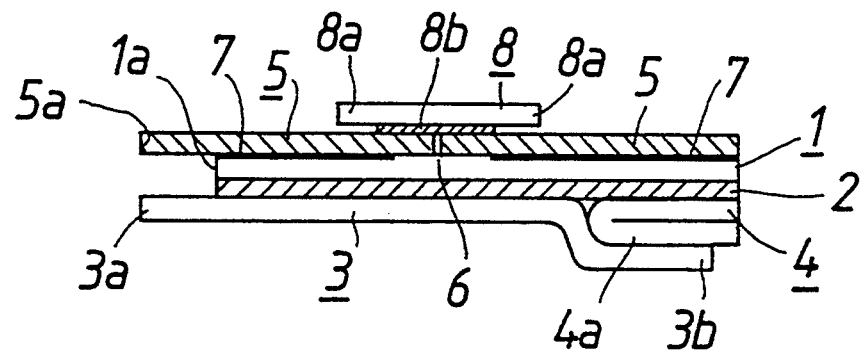
FIG. 1 is a longitudinal sectional view of the medical bandage.
Figure 2:
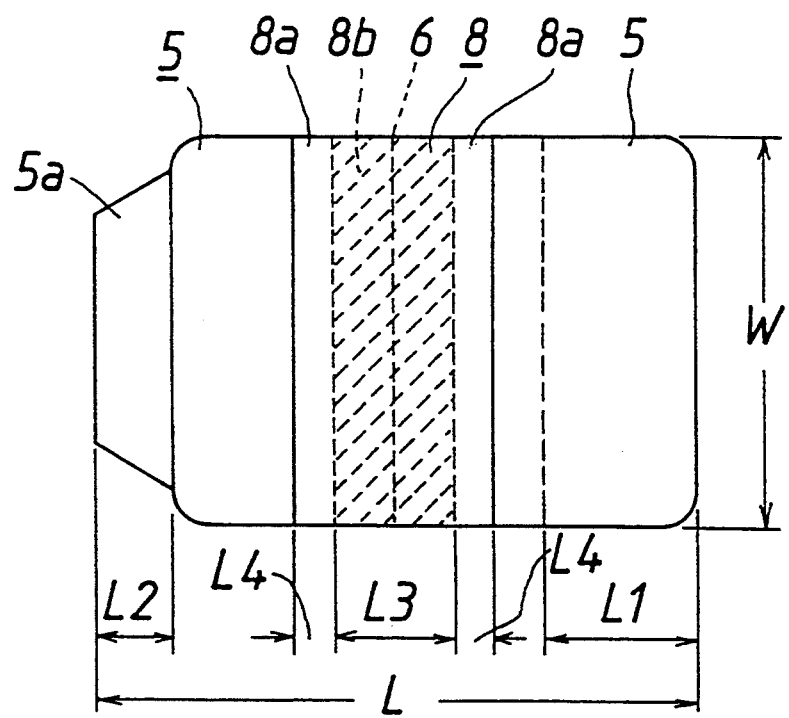
FIG. 2 is a plan view of the medical bandage.

An embodiment of the present invention will be described with reference to the accompanying drawings. FIGS. 1 and 2 are a longitudinal sectional view and a plan view, respectively, of the medical bandage of the present invention. There are shown a film-like or foil-like substrate 1, one end 1a of the substrate 1, a pressure-sensitive adhesive layer 2 formed on one side of the substrate 1, a release paper 3 placed on the pressure-sensitive adhesive layer 2, an extension part 3a of the release paper 3 which extends beyond the ends 1a of the substrate 1, a grasp strip 4 held under the other end 3b of the release paper 3, an extension part 4a of the grasp strip 4 which is folded back, a support 5 placed on the substrate 1 which is composed of two butted pieces of plastics film, an extension part 5a of the support 5 which extends beyond one end 1a of the substrate 1, a butting part 6 of the support 5, a fusion-bonded part 7 between the substrate 1 and the support 5, a support releasable strip 8 placed on the butting part 6 of the support 5 which is an adhesive plastics tape having non-adhesive parts on its both longitudinal sides, a non-adhesive part 8a of the releasable strip 8, and an adhesive part 8b of the releasable strip 8.

The medical bandage of the present invention has a substrate 1, as shown in FIG. 1. The substrate is in the form of foil or film, 10–100 μm thick, made of a thermoplastic resin which is capable of fusion-bonding but is releasable from the support 5. The thermoplastic resin is properly selected from polyethylene resin, polypropylene resin, polyvinyl chloride resin, polyurethane resin, polyamide resin, ethylene-vinyl acetate copolymer resin, polyester resin, polyvinyl alcohol resin, polyacrylate resin, polycarbonate resin, fluorine-containing resins, polystyrene resin, and polyvinylidene chloride resin. Of these, polyurethane resin is most suitable because of its permeability and fusion-bondability. For the impermeable substrate, polyvinylidene chloride is desirable because of its high water-vapor impermeability.

The substrate 1 may be transparent, opaque, colorless, or colored. However, it should be transparent as a matter of course in the case where it is necessary to view the affected part through the bandage at the time of application.

The medical bandage of the present invention has the pressure-sensitive adhesive layer 2 on one side of the substrate 1. It is coated with an adhesive which is not irritant to the skin. Such an adhesive is composed mainly of any one of natural rubber, aqueous polymer emulsion, thermoplastic rubber, polyurethane, and polyacrylic ester copolymer. The adhesive may be dissolved in either water or solvent. The pressure-sensitive adhesive layer 2 should have an adhesive strength of 300–900 g/25 mm width to the skin of a patient. With an adhesive strength lower than 300 g/25 mm, the bandage will peel away due to sweating and movement of a patient. With an adhesive strength higher than 900 g/25 mm, the bandage will damage the affected part when it is peeled off or replaced.

The medical bandage of the present invention has the release paper 3 on the pressure-sensitive layer 2. The release paper 3 has, at one end thereof, an extension part 3a which extends beyond the end 1a of the substrate 1. The release paper 3 also has the other end 3a which holds thereunder (between the release paper and the pressure-sensitive layer 2) a grasp strip 4. The grasp strip 4 is in contact with the pressure-sensitive layer 2, with its extension part 4a folded back outward.

The release paper 3 may be any one which is commonly used for medical bandages. Preferred examples are silicone-treated kraft paper and glassine paper, and silicone-treated polyethylene-laminated kraft paper and glassine paper.

The peel strength between the release paper 3 and the pressure-sensitive layer 2 should be 2–10 g/25 mm width, preferably 2–5 g/25 mm width. With a peel strength lower than 2 g/25 mm, the release paper 3 will peel away during storage and transportation. With a peel strength higher than 10 g/25 mm, the release paper 3 will not be readily peeled off at the time of application or will undergo delamination at the time of peeling.

The grasp strip 4 held between the release paper 3 and the pressure-sensitive layer 2 may be made of the same material as the release paper 3. In addition, it should have the same peel strength as the release paper.

The grasp strip 4 should be in contact with the pressure-sensitive layer 2 over a length (L1) which is about 1–4 cm. In addition, it should have an extension part 4a which is about 1–4 cm long. If the length (L1) of the grasp strip 4 is less than 1 cm, it would be difficult to handle the bandage smoothly. (With the release paper removed, the bandage has to be held by the extension part 4a of the grasp strip 4 and the extension part 5a of the support 5.) If the length (L1) of the grasp strip 4 is greater than 4 cm, the grasp strip 4 is so large that the visual field is obstructed. The length (L1) should preferably be shorter than 25% of the overall length.

The length of the extension part 4a of the grasp strip 4 may be equal to or smaller than the length (L1). It should be moderate so as to prevent the extension part 4a from being inadvertently pulled away untimely at the time of application. The end 3b of the release paper 3 is so dimensioned that it does not exceed the length of the extension part 4a of the grasp strip 4.

On the back of the substrate 1 is the support 5. It consists of two pieces of plastics film which are butted (6) at right angles to the longitudinal direction (L). It has at least one extension part 5a which extends from its end beyond one end 1b of the substrate 1. It is peelably fusion-bonded to the back of the substrate 1 (except for the butting part 6). On the butting part 6 of the support 5 is the releasable strip 8 in the widthwise direction (W), which is an adhesive tape (of adequate width) having non-adhesive parts 8b on its both longitudinal sides.

The plastics film for the support 5 is 20–120 μm thick, and it is made of any known thermoplastic resin which can be fusion-bonded to but peeled off from the film-like or foil-like substrate 1. Examples of the thermoplastic resin include polyethylene, polypropylene, polyamide, polyvinyl chloride, and polyester. They are selected according to the material of the substrate 1. If the substrate 1 is made of polyurethane, the support 5 should preferably be made of polyester which is compatible with polyurethane.

According to the present invention, the support 5 is formed by butting two pieces of plastics film. The butting part 6 is not necessarily limited to the center of the substrate so long as it is within the range from about 1/5 to 4/5 of the length of the substrate 1 measured in its longitudinal direction from one end thereof. The support 5 is intended to be removed without pulling up the substrate which has been stuck to a patient. Therefore, the two films have to be peeled off toward the ends of the substrate.

The support 5 has an extension part 5a at one end thereof. It should be about 1–4 cm long (L2) so that it facilitates the application of the bandage as explained above in connection with the grasp strip 4.

The support 5 is peelably fusion-bonded to the back of the substrate 1, except for the butting part 6. The fusion-bonding should be performed such that it produces a peel strength greater than that between the release paper 3 and the pressure-sensitive layer 2 or between the grasp strip 4 and the pressure-sensitive layer 2, but smaller than that between the substrate 5 and the releasable strip 8. In other words, the peel strength between the support 5 and the substrate 1 should be 10–100 g/25 mm width, that between the release paper 3 and the pressure-sensitive layer 2 should be 2–10 g/25 mm width, and that between the support 5 and the releasable strip 8 should be 15–150 g/25 mm width. Their maximum value should not exceed one half the peel strength (300–900 g/25 mm) between the pressure-sensitive layer 2 and a patient. This condition is necessary so that the substrate 1 is not peeled off from a patient under any circumstance when the releasable strip and support are peeled off after the application of the bandage. If this condition is not met, there is a possibility that the substrate is peeled off from a patient who is in a sweat when the releasable strip and support are peeled off. The peel strength of the fusion-bonded part 7 should be stronger than that between the release paper 3 and the pressure-sensitive layer 2 or between the grasp strip 4 and the pressure-sensitive layer 2, so that the support 5 will not peel off from the substrate 1 when the release paper 4 or the grasp strip 4 is peeled off. The peel strength of the fusion-bonded part 7 should be weaker than that between the substrate 5 and the releasable strip 8, so that the releasable strip 8 will not peel off from the support 5 when the support 5 is peeled off from the substrate 1 by the aid of the non-adhesive parts 8a of the releasable strip 8. If the releasable strip 8 peels off first from the support 5, it would be impossible to peel off the support 5 from the substrate 1.

The adhesive tape for the releasable strip 8 should be 2–4 cm wide (L3+L4×s). The non-adhesive part 8a of the adhesive tape should be 0.5–2 cm wide (L4). The adhesive tape may be transparent, opaque, colorless, or colored. However, it should be transparent as a matter of course in the case where it is necessary to view the affected part through the bandage at the time of application.

The aforesaid medical bandage of the present invention is used in the following manner. First, the release paper 3 is peeled off from the pressure-sensitive layer 2 by holding the extension part 5a of the support 5 and the extension part 3a of the release paper 3 (or by holding the grasp strip 4 and the end of the release paper 3). Second, the bandage (together with the support) is applied to a patient by holding the extension part 4a of the grasp strip 4 and the extension part 5a of the support 5. Third, the grasp strip 4 is slowly peeled off toward its end by holding its extension part 4a. This step permits the substrate 1 to be secured to the patient without being wrinkled or pulled up. The support 2 is lightly and evenly pressed against the patient to ensure the sticking of the pressure-sensitive layer 2 to the patient. Finally, one half of the support 5 is peeled off from the substrate 1 in the direction from the butting part 6 toward the end by holding one of the non-adhesive parts 8a of the releasable strip 8 and the other half of the support 5 is peeled off in the direction from the butting part 6 to the opposite end by holding its intermediate non-adhesive part. The application of the bandage in this manner is very simple and safe.

APPLICATION EXAMPLES

The medical bandage of the present invention was evaluated by actual use of a sample as shown in FIGS. 1 and 2. It is composed basically of a substrate 1 of transparent polyurethane film, 70 mm long (L), 50 mm wide (W), and 30 $\mu$m thick, a pressure-sensitive adhesive layer 2 (20 $\mu$m thick) of acrylic adhesive formed on one side of the substrate 1, a release paper 3 (70 $\mu$m thick) placed on the pressure-sensitive layer 2, said release paper having an extension part 3a extending 10 mm (L2) beyond one end 1a of the substrate 1, and a grasp strip 4 which is in contact with the pressure-sensitive layer 2 over a distance of 20 mm (L1) inward from the end of the substrate 1 and which has an extension part 4a folded back (same 20 mm) outward, the grasp strip 4 being held down by the end 3b of the release paper 3. The bandage is further provided on the back of the substrate 1 with a support 5 consisting of two pieces of transparent polyester film having an extension part 5a extending 10 mm from one end thereof. The support (polyester film) is peelably fusion-bonded to the substrate 1 (polyurethane film), except for the butting part. To the butting part 6 is attached a releasable strip 8 (30 mm wide, L3+L4×2) of colored transparent polypropylene adhesive film having non-adhesive sides (7 mm, L4). Table 1 shows the results of evaluation by actual use of the sample.

TABLE 1

| | | |
|---|---|---|
| Performance n = 10 | Peel strength between the releasable strip and the substrate | 115 g/25 mm |
| | Peel strength between the support and the substrate | 50 g/25 mm |
| | Peel strength between the substrate and the release paper | 4 g/25 mm |
| | Peel strength between the pressure-sensitive layer and the adherend (Bakelite plate) | 520 g/25 mm |
| Test in practical use n = 10 | Adhesion to the human skin | Good without wrinkles |
| | Peeling of the support from the substrate | No pulling up of the substrate |
| | Peeling from the human body | Good without damage to wound or burned skin |

As Table 1 shows, the medical bandage of the present invention was very good in performance and practical use.

It has been demonstrated that the medical bandage of the present invention permits the support to be easily peeled off from the substrate applied to the wound skin without the substrate being pulled up. The medical bandage is protected from dust and dirt during storage owing to the support placed on the substrate. The medical bandage permits the doctor or nurse to view the affected part through it with a minimum of obstruction because the substrate is a transparent film and the opaque grasp strip does not exceed 25% of the overall length. The support can be peeled off toward the end from the butting part without the thin substrate applied to the wound skin being pulled up. When the support has been removed, the substrate is not tacky and hence does not attract dust because they are peelably fusion-bonded together.

What is claimed is:

1. An improved medical bandage of the type having a substrate of plastic film or foil, a pressure-sensitive adhesive layer formed on one side of said substrate, and a release paper placed on said pressure-sensitive adhesive layer, wherein the improvement comprises a support consisting of two pieces of plastics film which are butted in the widthwise direction at the middle in the longitudinal direction and are peelably fusion-bonded to the other side of said substrate, such that said support is peeled off at the butting part from said substrate after the bandage has been applied to a patient.

2. An improved medical bandage of the type having a substrate of plastic film or foil, a pressure-sensitive adhesive layer formed on one side of said substrate, and a release paper placed on said pressure-sensitive adhesive layer, with one end thereof extending beyond the substrate to form an extension part and with the other end thereof holding thereunder a grasp strip which is partly in contact with the pressure-sensitive adhesive layer over a certain length from the end of the substrate, with the remainder folded back outward, wherein the improvement comprises a support and a releasable strip for the support, said support consisting of two pieces of plastics film butted in the widthwise direction at the middle in the longitudinal direction on the other side of said substrate, with at least one end thereof extending beyond the end of the substrate to form an extension part, said support being peelably fusion-bonded to the substrate except for the butting part, said releasable strip being an adhesive tape of desired width stuck to the butting part in the same direction as the butting part, said adhesive tape having non-adhesive parts on its both longitudinal sides.

3. A medical bandage as claimed in claim 1 or 2, wherein the plastics film or foil constituting the substrate is a 10–100 $\mu$m thick polyurethane film or foil and the plastics film constituting the substrate is a 20–120 $\mu$m thick polyethylene terephthalate film.

4. A medical bandage as claimed in claim 1 or claim 2, wherein the support is butted at a position within approximately 1/5 to 4/5 of the length of the substrate measured from one end thereof in the longitudinal direction.

5. A medical bandage as claimed in any one of claim 1 or claim 2, wherein the support is fusion-bonded to the substrate such that the peel strength between them is greater than that between the release paper and the pressure-sensitive layer or between the grasp strip and the pressure-sensitive layer and is smaller than that between the support and the releasable strip for the support.

6. A medical bandage as claimed in claim 1 or claim 2, wherein the releasable strip is bonded to the support such that the peel strength between them is smaller than one half that between the pressure-sensitive layer and the adherend.

7. A medical bandage as claimed in claim 1 or claim 2, wherein the support is fusion-bonded to the substrate such that the peel strength between them is 10–100 g/25 mm width.

8. A medical bandage as claimed in claim 1 or claim 2, wherein the releasable strip is bonded to the support such that the peel strength between them is 15–150 g/25 mm width.

9. A method for applying a medical bandage of the type having a substrate, a pressure-sensitive adhesive layer formed on of said substrate, a release paper placed on said pressure-sensitive adhesive layer, with one end thereof extending beyond the substrate to form an extension part and with the other end thereof holding thereunder a grasp strip which is partly in contact with the pressure-sensitive adhesive layer over a certain length from the end of the substrate, with the remainder folded back outward, and a support and a releasable strip for the support, said support consisting of two pieces of plastic film butted in the width wise direction at the middle on a second side of said substrate with at least one end extending beyond the end of the substrate to form an extension part, comprising the steps of: removing the release paper, sticking the medical bandage together with the support to the adherend after the release paper is removed by holding the grasp strip and the extension part of the support 5, peeling off the grasp strip from the pressure-sensitive layer, lightly pressing the support against the adherend so as to secure the pressure-sensitive layer to the adherend, peeling off one half of the support at the butting part toward the end from the substrate by holding either of the non-adhesive part on both sides of the releasable strip, and peeling off the other half of the support at the butting part toward the end from the substrate by holding either of the non-adhesive part of the remaining releasable strip.

* * * * *